United States Patent [19]

Hilliard et al.

[11] Patent Number: 4,695,547

[45] Date of Patent: Sep. 22, 1987

[54] PROBE FOR ELECTROFUSION, ELECTROPORATION, OR LIKE PROCEDURE

[75] Inventors: Jeffrey L. Hilliard, 5256 El Cemonte, Davis, Calif. 95616; Maurice M. Moloney, Davis, Calif.

[73] Assignee: Jeffrey L. Hilliard, Davis, Calif.

[21] Appl. No.: 847,356

[22] Filed: Apr. 2, 1986

[51] Int. Cl.[4] ............................................. C12N 13/00
[52] U.S. Cl. .................................. 435/173; 435/289; 435/287; 204/242; 204/272
[58] Field of Search ............... 435/287, 289, 300, 317, 435/173, 817; 204/242, 131

[56] References Cited

U.S. PATENT DOCUMENTS

| | | | |
|---|---|---|---|
| 1,857,224 | 5/1932 | Webber et al. | 204/131 |
| 3,547,801 | 12/1970 | Paine | 204/272 X |
| 3,726,762 | 4/1973 | Puharich | 435/173 X |
| 3,798,755 | 3/1974 | Sandstrom | 204/242 X |
| 3,843,450 | 10/1974 | Saxholm | 435/287 X |
| 3,964,991 | 6/1976 | Sullins | 204/272 X |
| 4,346,172 | 8/1982 | Swartz | 435/173 X |
| 4,599,314 | 7/1986 | Shaml | 435/287 |

Primary Examiner—Larry Jones
Attorney, Agent, or Firm—Townsend and Townsend

[57] ABSTRACT

A probe and method for treating samples in a well tray. The probe is specially configured to engage the well, and when so engaged, to provide an electrode structure within the well. The probe comprises an outer electrode in the form of a metal ring having a diameter just slightly less than the inner diameter of the well, a center electrode in the form of a metal rod, and a non-conductive (typically clear plastic) cover that extends over the well and holds the electrodes coaxial with respect to each other and with respect to the well. A metal pin is rigidly connected to the ring and extends parallel to the ring axis. The rod and pin pass through the cover so that their upper ends are accessible for electrical connections. Electrical connections are made to the portions of the rod and the pin located above the cover. As a safety measure, the electrical connections are preferably hidden under a cap that threadably engages the top portion of the rod and overlies the cover.

13 Claims, 4 Drawing Figures

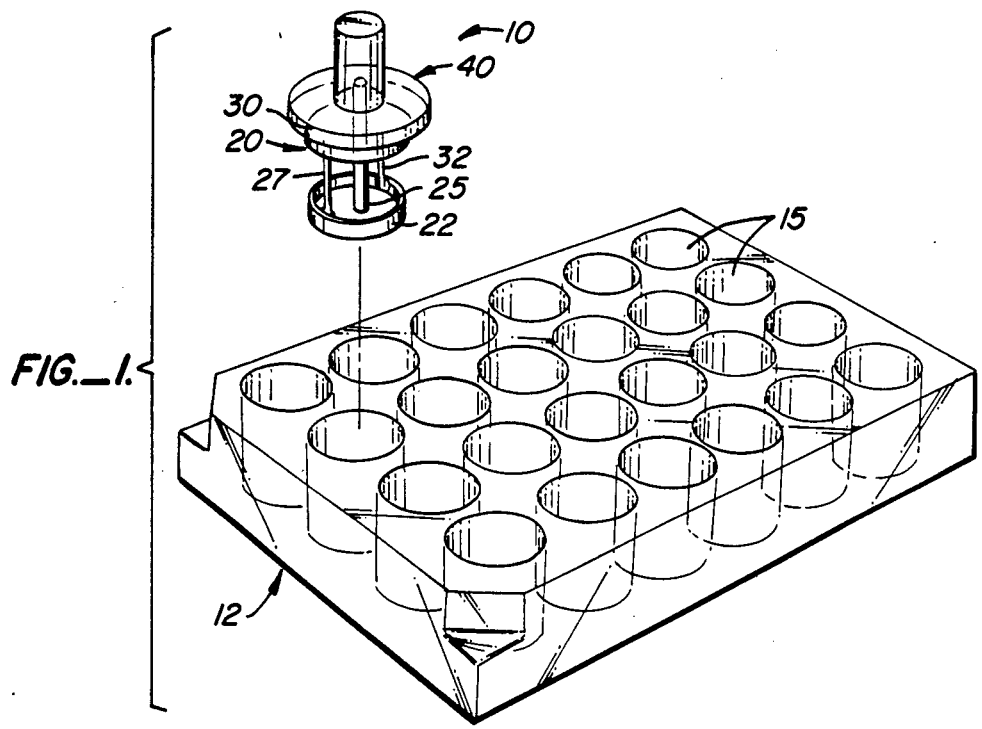
FIG._1.
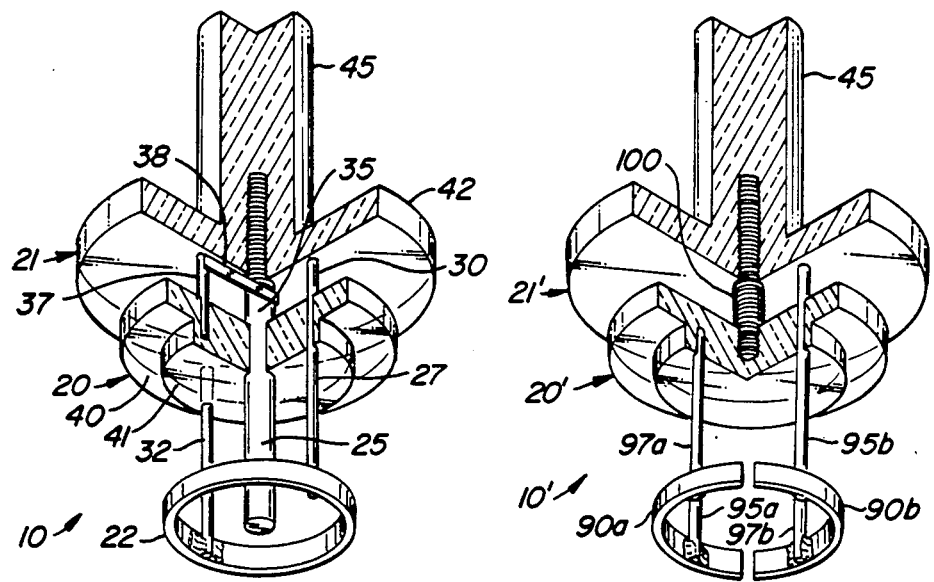
FIG._2. FIG._4.

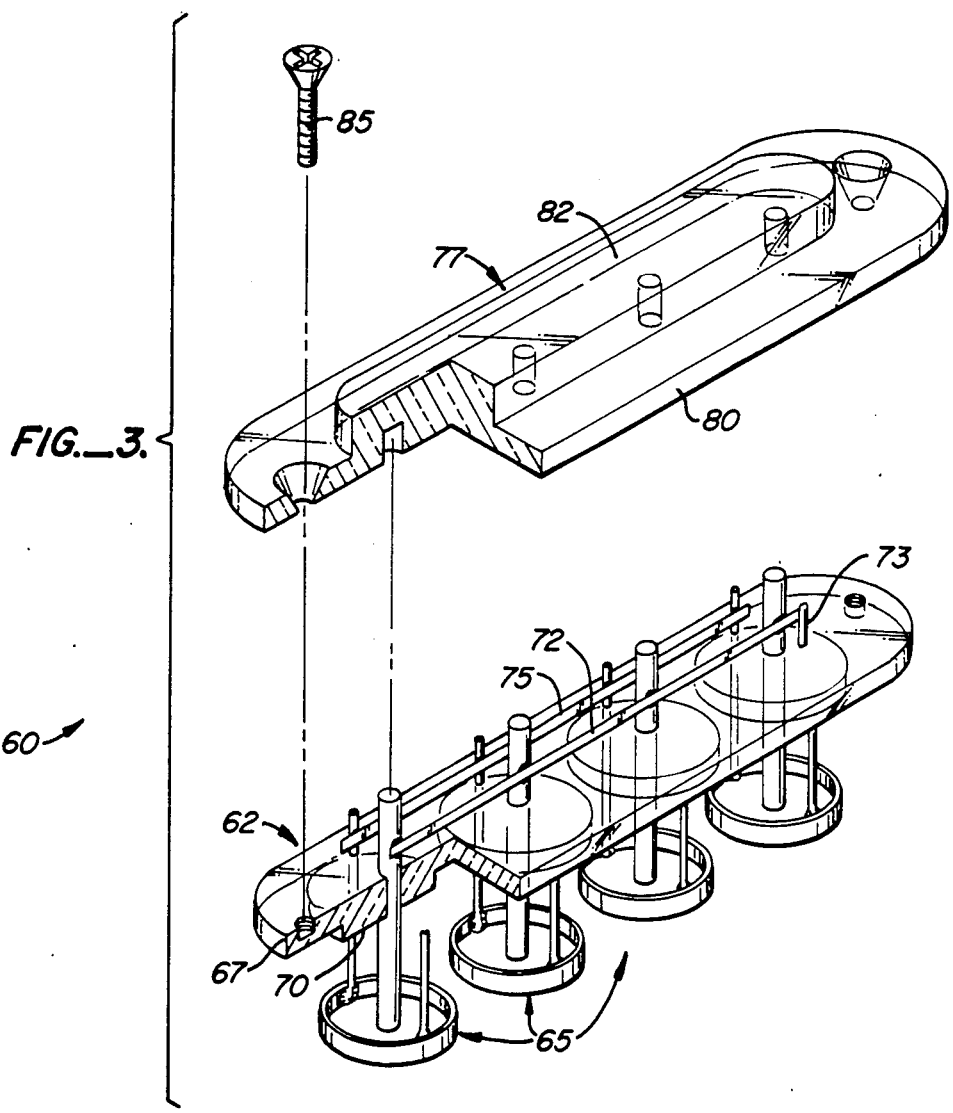

PROBE FOR ELECTROFUSION, ELECTROPORATION, OR LIKE PROCEDURE

FIELD OF THE INVENTION

The present invention relates generally to electrode structures, and more specifically to an electrode for treating samples of genetic material.

BACKGROUND OF THE INVENTION

A well tray comprises an array of cylindrical wells for storing and growing samples of genetic material. By way of example, a product marketed by Corning Glass Works, Corning, N.Y., under the trademark "CELL WELLS" comprises a 6×4 array of 16-mm diameter wells, each 18 mm deep. The well tray is molded of plastic such as clear polystyrene and has approximate outside dimensions of 85 mm×127 mm×22 mm.

Certain procedures such as electrofusion and electroporation require subjecting the samples to an electric field. Treating a sample entails withdrawing the sample froma flask or cuvette, placing the sample in a cell having suitably configured electrodes (called an electrode cell), treating the sample according to the desired procedure, removing the sample from the electrode cell, placing the sample in a well, and flushing the electrode cell to clean it for subsequent samples. Depending on the nature of the electrode cell, the cleaning step may represent a significant bottleneck in the process, and may present a risk of contamination.

SUMMARY OF THE INVENTION

The present invention provides a structure and method for treating samples in a well tray. Briefly, the invention contemplates the provision of a probe that is specially configured to engage the well, and when so engaged, to provide an electrode structurde within the well. The probe comprises an outer electrode in the form of a metal ring having a diameter just slightly less than the inner diameter f the well, a center electrode in the form of a metal rod, and a non-conductive (typically clear plastic) cover that extends over the well and holds the electrodes coaxial with respect to each other and with respect to the well.

A metal pin is rigidly connected to the ring and extends parallel to the ring axis. the rod and pin pass through the cover so that their upper ends are accessible for electrical connections. A second pin, also connected to the ring, may be provided to engage the cover in order to help maintain the ring coaxial with the rod.

The cover is preferably in the form of a flat portion extending beyond the edges of the well and one ormore projecting portions configured to engage the inner surface of the well. Thus, wehn the cover sits on top of the well, the projecting portions extend into the well and provide transverse registration to the well. In a preferred embodiment, the projecting portion is a single circular projection of a diameter slightly less than the well diameter.

Electrical connections are made to the portions of the rod and the pin located above the cover. As a safety measure, the electrical connections are preferably hidden under a cap that threadably engages the top portion of the rod and overlies the cover. Thus connection to the rod and pin can only be made from the side, with no metal portions exposed.

In a second embodiment, a single cover, large enough to span a plurality of wells, carries a corresponding plurality of electrode pairs spaced according to the well spacing. This allows multiple samples to be treated at one time. A bus bar arrangement connects all the rods to each other and all the pins to each other, so that only one set of electrical connections needs to be made.

An alternative embodiment utilizes a segmented ring configuration for the electrodes. A pair of electrodes, each consisting of a ring segment subtending slightly less than 180°, are held in opposed, coaxial alignment. Each ring segment is connected to one or more pins that engage the cover to keep the ring segment aligned. One pin for each ring segment extends through the cover for electrical connection.

The present inventio allows samples to be treated in the well, and provides a degree of efficiency and safety. The probe, which is cleaned between samples, is in general easier to clean than a cell with electrodes. The entire process may be conducted under sterile conditions and both the materials used and the electrode design facilitate maintenance of sterile environment. Therefore the process can be carried out quickly with minimal risk of inter-sample contamination. During the procedure, the cover prevents injury to nearby personnel in the event that a sample becomes overheated.

The present invention allows the samples to be visually observed during the procedure. Since the wells are normally made of transparent material, it is a simple matter to provide an inverted microscope and observe the sample from below. The electrode configuration contributes to this aspect of the invention since it does not block the view of the sample from below. In addition, the clear plastic cover facilitates light transmission which enhances observation.

A further understanding of the nature and advantages of the present invention may be realized by reference to the remaining portions of the specification and the attached drawings.

BRIEF DESCRIPTION OF THE DRAWINGS

FIG. 1 is a perspective view of the probe of the invention as used with a well tray;

FIG. 2 is a cutaway isometric view of the probe of FIG. 1;

FIG. 3 is an exploded cutaway isometric view of a multiple well embodiment of the invention; and FIG. 4 is a cutaway isometric view illustrating an alternative electrode structure.

DESCRIPTION OF THE PREFERRED EMBODIMENTS

FIG. 1 is a perspective view, taken from above, of a probe 10 according to the present invention. Probe 10 is used with a well tray 12 for subjecting a sample of genetic material to an operation such as electrofusion and electroporation. Well tray 12 is a molded plastic (typically clear polystyrene) structure that provides a plurality of cylindrical wells 15 designed to hold samples. The particular embodiments of the probe described herein are configured for use with wells having a 16-mm inner diameter. The particular well tray shown has 24 wells, disposed in a 6×4 array on 19-mm centers. In use, probe 10 engages one of wells 15, and when so engaged, provides an electrode structure disposed to subject a sample of genetic material in the well to an electric field. For purposes of description, well tray 12 will be assumed horizontal with wells 15 opening upwardly.

FIG. 2 is a cutaway view, taken from below, illustrating the preferred construction of probe 10. Probe 10 comprises a plastic cover 20, an electrode structure mounted beneath the cover with terminals above the cover, and a cap 21 overlying the cover and terminals. Although many materials could be used, clear polished polycarbonate is preferred for the plastic parts and stainless steel with silver soldered connections is preferred for the electrodes. The electrode structures includes an outer electrode in the form of a thin-walled ring 22 and a central or inner electrode in the form of a rod 25.

Ring 22 has an outer diameter slightly less than the inner diameter of wells 15; for 16-mm wells, a 15.5-mm ring diameter and a 0.6-mm wall thickness are appropriate. The axial height of ring 22 is chosen to be commensurate with the depth occupied by the sample. The illustrated embodiments have a 2.5-mm height for the ring. Ring 22 is rigidly and electrically connected to a pin 27, which extends parallel to the ring axis and passes through cover 20 with a portion 30 protruding above the cover. A second pin 32 is rigidly connected to ring 22 at a point generally opposite that at which pin 27 is connected, and engages the cover but does not pass through it.

Rod 25 extends coaxially with respect to ring 25 and passes through the cover with a portion 35 protruding above the cover. Rod 25 has a diameter of about 2.5-mm and is preferably threaded at its upper end. A short pin 37 is inserted into cover 20 from above but does not pass through it, and is electrically connected to rod 25 by a strap 38.

Cover 20 includes a flat portion 40 and a downwardly projecting portion 41. Flat portion 40 is sized to extend beyond the edges of the well, and is circular in the preferred embodiment. Projecting portion 41 is configured to register the cover to the wells, and is preferably circular with a diameter sized for a close sliding fit within the well. A 15.8-mm diameter is appropriate for the 16-mm diameter wells in question. Cap 21 is threaded onto the upper end of rod 25, and is spaced above cover 20 by about 5 mm. The cap includes a flat circular portion 42 and an upstanding handle 45.

In use, the probe is placed with ring 22 and rod 25 in one of wells 15 and cover 20 overlying the well. The axial dimensions of the rod and pins are such that cover 20 rests atop the well and the lower edge of ring 22 and the lower end of rod 25 are just above the well bottom. Pin portion 30 and rod portion 32, being accessible above the top of the well, provide electrical terminals for connection to a pulsed power supply for carrying out the procedure in question. Cap 21 covers the terminals so that they are accessible only from the side, thereby reducing possible shock hazard.

FIG. 3 is an exploded cutaway isometric view of a probe 60 suitable for treating several samples at once. A single cover 62 carries a plurality of electrode pairs 65 disposed to engage a plurality of wells. These need not be adjacent wells, although normally the spacing is such as to accommodate adjacent wells. Cover 62 comprises a racetrack-shaped flat portn 67 with downwardly projecting circular portions 70 configured to register the cover, and hence the probe, with the wells.

Each electrode pair may be substantially as described above in connection with probe 10 of FIGS. 1 and 2, with the rod electrodes extending through the cover and each of the ring electrodes being supported on a pair of pins, one of which extends through the cover. Electrical connections are provided so that all the ring electrodes are connected and all the rod electrodes are connected. To this end, a strap 72 is connected to all the rods and terminates at a short pin 73 which penetrates the cover from above but does not extend through it, while a second strap 75 connects all the projecting pin portions. A cap 77 overlies the electrodes and includes a racetrack-shaped flat portion 80 extending outwardly beyond the confines of the cover, and an upstanding handle portion 82. In the preferred embodiment, cap 77 is provided with blind holes that accommodate the ends of the rods. These are sized for a slip fit with the actual connection being effected by insulating screws.

FIG. 4 is a cutaway isometric view, taken from below, showing an alternate electrode structure that may be used with the single-well embodiment of FIGS. 1 and 2 or the multi-well embodiment of FIG. 3. The electrodes are shown in a single-well probe 10', with a cover 20' and a cap 21' corresponding to cover 20 and cap 21 of probe 10. In this case, there is no rod, but rather the two electrodes are defined by semiannular segments 90a and 90b, each of which is slightly less than half of the full ring. Segment 90a is supported on a similar pair of pins 95b and 97b. Pins 95a–b extend through the cover while pins 97a–b terminate in blind holes in the cover. Cap 21' is spaced above cover 20' by a threaded insulated shaft 100 which threadably engages both the cover and the cap.

In use, the probe is inserted into one or several wells containing genetic material, a pulsed power supply is connected to the terminals located under the cap, and a voltage pulse is applied. A typical application of the probe is the introduction of foreign macromolecules (nucleic acids and proteins) into target cells in the sample. Factors that are likely to influence the procedure include the pulse voltage (actually the electric field) and the pulse length, as well as electrolyte and macromolecule concentrations and target cell density. A suitable source of high voltage pulses is marketed under the trademark "Proto Blaster" by Compudigital Industries, Davis, Calif., and is capable of providing output voltage pulses in the range of 25–475 volts DC at currents up to 1 amp and durations of 1–990 ms.

The probe of the invention is easy to clean between samples. When it is removed from the well, it can be cleaned in alcohol and rinsed with distilled water. This procedure may be used to ensure that all manipulations take place under aseptic conditions. A significant advantage of treating the samples in the wells with the probe is that the sample may be viewed from the bottom of the well. The well trays are made of clear material and the electrode structure, being a coaxial configuration, does not obscure the sample. Thus, by placing the well tray on a transparent table and viewing it from below with an inverted microscope allows direct observation of the procedure. The probe cover and cap, being clear, allow the sample to be illuminated from above.

In conclusion it can be seen that the probe of the present invention facilitates a number of procedures. The probe is simple, easy to clean, appropriate for work under sterile conditions, and capable of relatively inexpensive manufacture.

While the above is a complete disclosure of the preferred embodiments, various modifications, alternate constructions, and equivalents may be used. For example, the use of two pins to support the ring electrode provides a rigid coaxial structure regardless of whether the probe is inserted into the well or not. However, a single pin, while it would not guarantee the coaxial alignment when the probe is outside the well (the ring could rotate about the pin axis), the well itself would maintain the ring coaxial with the circular projection on the cover, which would then maintain the rod coaxial within the ring. Thus, the required coaxial alignment would be provided. Similarly, while a circular projection on the cover is disclosed, there is no requirement that the projection be circular, or that there be a projection at all. Indeed, with two pins supporting the ring electrode, the coaxial alignment of the cover with the well is guaranteed. Moreover, while the overlying cap allows the electrical connections to be effected with alligator clips and still prevent any exposed metal, the cap could be dispensed with if a special cable connector, configured to engage the upper pin portion and upper rod portion were provided.

Therefore, the above description and illustrations should not be taken as limiting the scope of the present invention which is defined by the appended claims.

We claim:

1. A probe for insertion into a cylindrical well for subjecting a sample of genetic material in the well to the action of an electric field, comprising:
    a metal ring having an outer diameter slightly less than the inner diameter of the well to permit free insertion of said ring into the well coaxial with respect to the well;
    a cover;
    a metal rod having an outer diameter less than the inner diameter of said ring and extending through said cover such that one end of said rod defines a first electrical terminal above said cover and the other end of said rod is proximate the bottom of the well when the probe is inserted into the well; and
    a metal pin extending through said cover and having a first end defining a second electrical terminal above said cover and a second end rigidly and electrically joined to said ring such that the lower edge of said ring is proximate the bottom of the well when the probe is inserted into the well;
    said cover holding said rod coaxial with respect to the well when said ring is inserted into the well coaxial with respect to the well.

2. The probe of claim 1 wherein said cover has a flat portion extending beyond the well opening and a projecting portion configured to engage the inner wall of the well to provide lateral registration.

3. The probe of claim 1 further comprising a second pin joined to said ring and to said cover for holding said ring coaxial with said rod regardless of whether the probe is inserted in the well or not.

4. A probe for insertion into a cylindrical well for subjecting a sample of genetic material in the well to the action of an electric field, comprising:
    a metal ring having an outr diameter slightly less than the inner diameter of the well to permit free insertion of said ring into the well coaxial with respect to the well;
    a metal rod having first and second ends spaced by a distance greater than the well depth and having an outer diameter less than the inner diameter of said ring;
    a metal pin having a first end rigidly and electrically joined to said ring and a second end spaced from the first end by a distance greater than the well depth; and
    cover means having a first hole sized to capture said rod in a region between the first and second ends thereof for holding said rod coaxial with respect to the well with the first end of said rod substantially at the bottom of the well, and the second end of said rod above the top of the well and accessible for electrical connection;
    said cover means further having a secondhole sized to capture said pin in a region between the first and second ends thereof for holding said ring generally flush with the first end of said rod, the second end of said pin defining an electrical terminal above the top of the well for establishing an electrical path betwen said ring and said electrical terminal.

5. The probe of claim 4 wherein said pin extends parallel to the axis of said ring.

6. The probe of claim 4 further comprising:
    an additional pin having a first end rigidly attached to said ring and a second end rigidly attached to said cover means.

7. The probe of claim 4 wherein said cover means has a flat portion extending beyond the well opening and a circular projecting portion of diameter slightly less than the well diameter, whereupon said circular portion maintains said cover means laterally registered with said well.

8. The probe of claim 7 wherein said pin extends parallel to said rod.

9. The probe of claim 7 wherein said ring, said rod, and said pin are stainless steel, and wherein said cover is plastic.

10. The probe of claim 4, and further comprising:
    a cap connected to the second end of said rod and extending radially outwardly therefrom so as to overlie said electrical terminal and prevent access to said rod and said electrical terminal from above while allowing access to said rod and said electrical terminal from the side, thereby providing a measure of protection from electrical shock.

11. The probe of claim 10, and further comprising electrical lead-out means, connected to said rod, defining an additional electrical terminal radially outboard of said rod.

12. The probe of claim 10 wherein said rod is formed with threads at the second end thereof, and wherein said cap threadably engages said rod.

13. A probe for insertion into a well tray for subjecting a plurality of samples of genetic material in a corresponding plurality of cylindrical wells in the well tray tot he action of an electric field, comprising:
    a plurality of electrode pairs, each comprising a metal ring having an outer diameter slightly less than the inner diameter of the wells and a metal rod having an outer diameter less than the inner diameter of the ring;
    means for holding said rods in spaced parallel alignment, with said rods on axes spaced corresponding to the axes of the plurality of wells;
    means for maintaining said rod and ring pairs in respective coaxial alignment with respect to each other and with respect to a corresponding well when said rings are in said wells; and
    electrical connection means for establishing a first electrical terminal connected to said rings and a second electrical terminal connected to said rods.

* * * * *